US008911779B2

United States Patent
Kitajima et al.

(10) Patent No.: US 8,911,779 B2
(45) Date of Patent: Dec. 16, 2014

(54) TABLET AND PESTLE THEREFOR

(75) Inventors: Hideaki Kitajima, Kagawa (JP); Shiro Horie, Kagawa (JP)

(73) Assignee: Kyowa Chemical Industry Co., Ltd., Takamatsu-shi (JP)

( * ) Notice: Subject to any disclaimer, the term of this patent is extended or adjusted under 35 U.S.C. 154(b) by 0 days.

(21) Appl. No.: 13/264,163

(22) PCT Filed: Apr. 20, 2010

(86) PCT No.: PCT/JP2010/056992
§ 371 (c)(1),
(2), (4) Date: Oct. 13, 2011

(87) PCT Pub. No.: WO2010/122996
PCT Pub. Date: Oct. 28, 2010

(65) Prior Publication Data
US 2012/0034301 A1 Feb. 9, 2012

(30) Foreign Application Priority Data

Apr. 22, 2009 (JP) .................. 2009-104097

(51) Int. Cl.
*A61K 9/20* (2006.01)
*A61J 3/10* (2006.01)
*B30B 15/06* (2006.01)

(52) U.S. Cl.
CPC ................. *B30B 15/065* (2013.01); *A61J 3/10* (2013.01); *A61K 9/2077* (2013.01)
USPC .......................................... 424/464; 425/400

(58) Field of Classification Search
CPC ........ A61J 3/10; B30B 15/065; A61K 9/2077
USPC ........................................... 424/464; 425/400
See application file for complete search history.

(56) References Cited

U.S. PATENT DOCUMENTS 4,376,111 A 3/1983 Tovey
6,436,447 B1 8/2002 Inoue et al.
(Continued)

FOREIGN PATENT DOCUMENTS

EP 0 070 720 A1 1/1983
JP 49-37026 10/1974
(Continued)

OTHER PUBLICATIONS

International Preliminary Report on Patentability for PCT/JP2010/056992 (World Intellectual Property Organization, Nov. 22, 2011) (English Translation), 6 pages.*

(Continued)

*Primary Examiner* — Jason Sims
*Assistant Examiner* — Miriam A Levin
(74) *Attorney, Agent, or Firm* — Birch, Stewart, Kolasch & Birch, LLP

(57) ABSTRACT

A tablet which comprises solid particles, especially magnesium oxide particles as the main component and has excellent shape retentivity with extremely low susceptibility to wearing and chipping. The tablet has a domed shape on each of the upper and lower horizontal surfaces of a cylindrical plate shape, wherein the domed shape on each of the upper and lower horizontal surfaces satisfies the following requirements (a), (b) and (c) in the cross-sectional shape including the center line of the cylindrical plate shape: (a) each corner has an angle of 25 to 45°, (b) each corner has a horizontal length of 0.30 to 1.0 mm, and (c) the cup has a depth of 0.6 to 1.2 mm.

10 Claims, 2 Drawing Sheets

(56) References Cited

U.S. PATENT DOCUMENTS

| | | | |
|---|---|---|---|
| 7,147,868 B2 | 12/2006 | Sofue et al. | |
| 2004/0022872 A1 | 2/2004 | Sofue et al. | |
| 2009/0148520 A1* | 6/2009 | Arima et al. | 424/464 |

FOREIGN PATENT DOCUMENTS

| | | |
|---|---|---|
| JP | 9-40561 A | 2/1997 |
| JP | 2000-1428 A | 1/2000 |
| JP | 2001-48792 A | 2/2001 |
| JP | 2003-146889 A | 5/2003 |
| WO | WO 2007/007659 A1 | 1/2007 |

OTHER PUBLICATIONS

International Search Report for PCT/JP2010/056992 (World Intellectual Property Organization, Jun. 1, 2010) (English Translation), 4 pages.*

U.S. Pharmacopeia, General Chapter <1216> Tablet Friability [Retrieved from internet <URL: http://www.pharmacopeia.cn/v29240/usp29nf24s0_c1216.html >] [Downloaded Mar. 12, 2014], 2 pages.*

International Search Report, dated Jun. 1, 2010, issued in PCT/JP2010/056992.

Kigasawa et al., "Pharmaceutical Studies on Physical Properties of Solid Form Drugs. III. Influence on Tablet Formula and Tablet Shape on Distribution of Boring Hardness inside Tablet", Journal of the Pharmaceutical Society of Japan, vol. 95, No. 7, pp. 769-773, 1975.

Ueno, "Kine Usu no Sekkei to Seisaku", Pharm Tech Japan, vol. 11, No. 5, pp. 549-552, 1995.

Extended European Search Report for Appl. No. 10767053.1 dated Jan. 22, 2014.

Japanese Office Action for corresponding Japanese Application No. 2011-510321 dated Mar. 18, 2014.

Partial English translation (explanation of the drawings) for UENO, "Kine Usu no Sekkei to Seisaku", Pharm Tech Japan, vol. 11, No. 5, pp. 549-552, 1995.

* cited by examiner

TABLET AND PESTLE THEREFOR

TECHNICAL FIELD

The present invention relates to a tablet having a specific shape and a pestle used to make the tablet. More specifically, it relates to a tablet which has a high content of solid particles and is compression molded and physically stable with extremely low susceptibility to wearing and chipping and to a pestle used to obtain the tablet. Much more specifically, it relates to a tablet which has a high content of magnesium oxide particles and extremely low susceptibility to wearing and chipping.

BACKGROUND ART

Heretofore, tablets for oral administration which have a circular (spherical, disk-like) shape or an irregular (football-like, oval or triangular) shape have been commercially available. To tablet magnesium oxide particles, for example, there are known methods of tableting a blend of magnesium oxide particles, a binder and a disintegrating agent (Patent Documents 1 and 2). Since the tablets obtained by these methods have relatively high contents of the binder and the disintegrating agent, the content of the magnesium oxide particles in the tablets is not so high. These tablets have a long disintegration time in the oral cavity and are difficult to be taken when they are administered orally.

In contrast to this, there is proposed a tablet which has a high content of magnesium oxide particles and a short disintegration time (Patent Document 3). This tablet contains 88 to 97 wt % of magnesium oxide particles, has a very short disintegration time of less than 10 seconds and is easy to be taken. This Patent Document 3 teaches that this tablet has a diameter of 5 to 12 mm and a thickness of 2 to 6 mm but is silent about its shape.

PRIOR ART DOCUMENTS

Patent Documents

Patent Document 1: JP-A 9-40561
Patent Document 2: JP-A 2001-48792
Patent Document 3: JP-A 2003-146889

OUTLINE OF THE INVENTION

Problems that the Invention is to Solve

It is an object of the present invention to provide a tablet which has a high content of solid particles and excellent shape retention stability with low susceptibility to wearing and chipping in tableting, packaging and transport processes.

It is another object of the present invention to provide a tablet which has a high content of magnesium oxide particles, high hardness and excellent shape retentivity with extremely low susceptibility to wearing and chipping in tableting, transportation and packaging processes and during storage as well as a tableting pestle therefor.

According to studies conducted by the inventors of the present invention, it was found that the above objects of the present invention are attained by a tablet which has a cylindrical plate basic skeleton, a domed shape on each of the upper and lower horizontal surfaces of the basic skeleton, and (a) a specific corner angle, (b) a specific corner horizontal length and (c) a specific cup depth in the cross-sectional shape including a center line. The present invention was accomplished based on this finding.

Means for Solving the Problems

According to the present invention, there is provided a tablet which has a domed shape on each of the upper and lower horizontal surfaces of a cylindrical plate shape, wherein the domed shape on each of the upper and lower horizontal surfaces satisfies the following requirements (a), (b) and (c) in the cross-sectional shape including the center line of the cylindrical plate shape:
(a) each corner has an angle of 25 to 45°,
(b) each corner has a horizontal length of 0.30 to 1.0 mm, and
(c) the cup has a depth of 0.6 to 1.2 mm.

According to the present invention, there is provided a pestle for tableting solid particles, which satisfies the following requirements (a), (b) and (c):
(a) each corner has an angle of 25 to 45°,
(b) each corner has a horizontal length of 0.30 to 1.0 mm, and
(c) the cup has a depth of 0.6 to 1.2 mm.

Further, in the present invention, it is desired that the tablet should have the following features:
(1) (a) each corner has an angle of 28 to 40°,
(2) (b) each corner has a horizontal length of 0.35 to 0.85 mm,
(3) (c) the cup has a depth of 0.65 to 1.1 mm,
(4) the length (diameter) of the horizontal surface of the cross-sectional shape is 7 to 11 mm,
(5) the tablet comprises magnesium oxide particles represented by the following formula (1) as the main component:

$$(Mg_{1-x}Zn_x)O \qquad (1)$$

(x is 0 to 0.3.),
(6) the content of the magnesium oxide particles is 85 to 95 wt %,
(7) the tablet comprises magnesium oxide particles having an average secondary particle diameter of 0.5 to 25 μm as the main component,
(8) the tablet is administered orally,
(9) the tablet is used for laxative purpose, and
(10) the tablet is used for laxative purpose and administered orally.
It is desirable that the pestle of the present invention should be used to tablet magnesium oxide particles.

Effects of the Invention

According to the present invention, there can be provided a tablet which has a high content of solid particles, especially magnesium oxide particles, is compression molded and is provided with excellent shape retention stability with extremely low susceptibility to wearing and chipping in compression tableting, transportation, storage, packaging and sales processes by specifying its shape. The tablet comprising magnesium oxide particles according to the present invention can have a high content of magnesium oxide particles, is extremely excellent in shape stability, and is easy to betaken with a very short disintegration time when it is administered orally.

MODE FOR CARRYING OUT THE INVENTION

The shape of the tablet of the present invention will be described with reference to the accompanying drawings.

Figure 1:
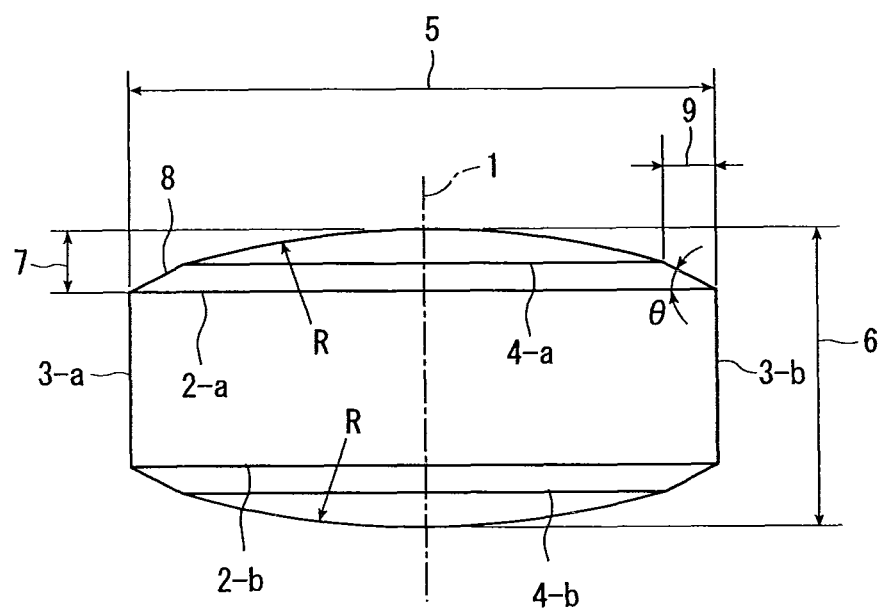
FIG. 1 shows the cross-sectional structure in the vertical direction along the center line of the cylindrical plate shape of the tablet of the present invention.

FIG. 1 shows the cross-sectional structure in the vertical direction along the center line 1 of the cylindrical plate shape of the tablet of the present invention. As shown in FIG. 1, the cross-sectional structure in the vertical direction (may be simply referred to as "cross-sectional shape" hereinafter) along the center line of the tablet of the present invention is bilaterally symmetric with the center line 1 as the center axis, and the cylindrical plate shape has a quadrilateral basic skeleton composed of four sides which are an upper horizontal surface 2-a, a lower horizontal surface 2-b, a surrounding side surface 3-a and a surrounding side surface 3-b and also a domed shape on the upper horizontal surface 2-a of this basic skeleton and a domed shape on the lower horizontal surface 2-b. The domed shape on the upper horizontal surface and the domed shape on the lower horizontal surface are identical to each other in the vertical direction.

The tablet of the present invention has the following features (a) to (e) in the cross-sectional shape:
(a) the tablet has a quadrilateral basic skeleton based on a cylindrical plate shape (the basic skeleton portion has a round disk-like shape),
(b) the angle θ between each of the linear sides 8 of the domed shape from the end of the upper horizontal surface 2-a and the horizontal surface (to be referred to as "corner angle") is 25 to 45°,
(c) the distance 9 projected on the upper horizontal surface of the length of each of the linear sides 8 having the above corner angle (to be referred to as "corner horizontal length") is 0.35 to 0.85 mm,
(d) the length 7 of the center line from the upper horizontal surface to the apex of the domed shape (to be referred to as "cup depth") is 0.65 to 1.1 mm, and
(e) the tablet is bilaterally symmetric with the center line 1 as the center axis, and the domed shapes on the upper horizontal surface and on the lower horizontal surface are symmetric in the vertical direction.

Further, in the cross-sectional shape of the tablet of the present invention, the domed shape formed on an upper dome horizontal surface 4-a is desirably part of a circle having a single curvature R (to be referred to as "curvature R"), and the radius of the curvature R is 7 to 25 mm, preferably 8 to 22 mm.

The tablet of the present invention is characterized in that it has a cross-sectional shape and a length shown in (a) to (e).

Out of these, each corner has an angle θ of 25 to 45°, preferably 28 to 40°, particularly preferably 29 to 33°. It is important that the sides 8 from both ends of the horizontal surfaces forming this corner angle should be linear and should have a constant length.

That is, the cross-sectional shape of the tablet of the present invention is characterized in that each of the domed shapes formed on the upper and lower horizontal surfaces has a two-stage structure consisting of linear portions (linear sides 8) from both ends of the horizontal surface and part of a circle having a curvature R.

The tablet which has a strong shape as air is smoothly removed therefrom by the compression of the solid particles at the time of tableting due to this two-stage structure has extremely low susceptibility to wearing and chipping caused by an impact and contact between tablets. As obvious from Comparative Examples which will be given hereinafter, when a tablet having domed shapes which have a curve directly from both ends of the horizontal surfaces is made, even if the angle of each of the domed shapes is about 30°, the removal of air does not occur fully and a tablet which is susceptible to wearing and chipping is obtained.

The tablet of the present invention has a corner horizontal length 9 of 0.3 to 1.0 mm, preferably 0.35 to 0.85 mm. The cup depth 7 is 0.6 to 1.2 mm, preferably 0.65 to 1.1 mm.

The tablet of the present invention comprises solid particles as the main component and has a weight of about 200 to about 600 mg each. As for the size of the tablet of the present invention, the weight of the tablet can be changed by varying its thickness and diameter. The diameter 5 (the length of each of the upper and lower horizontal surfaces) of the tablet is 6 to 14 mm, preferably 7 to 11 mm, and the thickness 6 of the tablet is 4 to 6 mm, preferably 4.2 to 5.6 mm. The diameter 5 and the thickness 6 may be suitably determined from the above ranges based on the desired weight of each tablet.

The tablet of the present invention comprises solid particles as the main component, a product obtained by compression molding fine powders of the particles is suitable, and a compressed molded product of powders containing magnesium oxide particles as the main component is particularly suitable. A description is subsequently given of a tablet comprising magnesium oxide particles as the main component The magnesium oxide particles are suitably contained in the tablet as the main component in an amount of not less than 80 wt %, preferably 85 to 95 wt %, particularly preferably 87 to 93 wt %. The magnesium oxide particles themselves are an active component, and as the content of the magnesium oxide particles in one tablet becomes higher, it is possible to reduce the size and number of tablets to be administered each time more The magnesium oxide particles may be particles of a compound represented by the following chemical formula (1). That is, they may be magnesium oxide particles comprising a small amount of a solid solution of zinc.

$$(Mg_{1-x}Zn_x)O \qquad (1)$$

In the above formula, x is 0 to 0.3, preferably 0 to 0.2.

It is advantageous that magnesium oxide particles having an average secondary particle diameter measured by a laser diffraction scattering method of 0.5 to 25 μm, preferably 0.5 to 10 μm, particularly preferably 1 to 7 μm should be used. The average secondary particle diameter of magnesium oxide is connected with the content of magnesium oxide particles in the tablet, the hardness of the tablet, and wearing and chipping. A preferred range out of the above range is suitable.

The tablet comprising magnesium oxide particles as the main component becomes a tablet which has lower susceptibility to wearing and chipping and a shorter disintegration time when it is administered by suitably selecting the types and amounts of a binder and a disintegrating agent as additives. The binder is preferably selected from crystalline cellulose and starch (such as corn starch) and is contained in the tablet in an amount of 1 to 10 wt %, preferably 1 to 8 wt %. The disintegrating agent is preferably selected from croscarmellose sodium, carmellose calcium and sodium carboxy starch, particular preferably croscarmellose sodium. The disintegrating agent is contained in the tablet in an amount of 1 to 3.5 wt %, preferably 1 to 3 wt %.

To make the tablet comprising magnesium oxide particles as the main component, magnesium oxide particles having the above average secondary particle diameter in a powder form or granular form are mixed with a binder and a disintegrating agent to prepare a mixed powder (or mixed granule) which is compression tableted to obtain a tablet having a predetermined shape.

As for pestles used for tableting, the corner angle, corner horizontal length and cup depth at the ends of an upper pestle and a lower pestle are adjusted to obtain the shape of the tablet of the present invention.

When the tablet comprising magnesium oxide particles as the main component according to the present invention contains the above ranges of the amounts of the above magnesium oxide particles, the above binder and the disintegrating agent, it can be molded with a relatively low pressure, the abrasion of the tableting pestle is little, and the obtained tablet has extremely low susceptibility to wearing and chipping.

According to the present invention, there is provided the shape of a pestle for making a tablet having the above specific shape.

Figure 2:
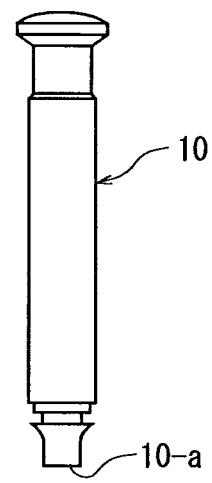
FIG. 2 shows the sectional structure of a pestle for making the tablet of the present invention, which comprises an upper pestle, a mortar and a lower pestle.
Figure 2:
Figure 2:
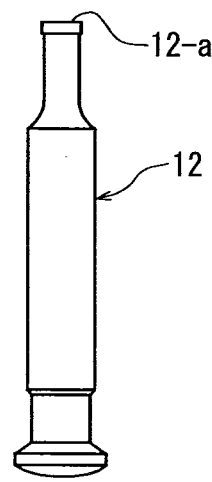

FIG. 2 shows an upper pestle 10, a mortar 11 and a lower pestle 12 for tableting. The shape of an end (10-a) of the upper pestle 10 is reversely concave so that a portion above the upper horizontal surface of the tablet shown in FIG. 1 is molded. That is, it is reversely concave so that a tablet having a specific corner angle, a specific corner horizontal length and a specific cup depth is obtained.

Meanwhile, an end (12-a) of the lower pestle is concave so that a portion below the lower horizontal surface of the tablet shown in FIG. 1 is molded. The mortar 11 has a cylindrical hollow having a long diameter corresponding to the circular shape of the tablet.

As for the shape of the pestle, portions other than the end (10-a) of the upper pestle and the end (12-a) of the lower pestle which correspond to the shape of the tablet of the present invention have a pestle structure that is commonly used.

EXAMPLES

The following examples are provided to further illustrate the present invention.

In the examples, (a) hardness, (b) disintegrating time, (c) degree of wearing and (d) thickness of the tablet are values measured by the following methods.

(a) Hardness

The hardness of the tablet was measured by using the DC-50 tablet hardness meter (of Okada Seiko Co., Ltd.).

(b) Disintegration Time

This was measured by using water as a test liquid in accordance with the "general test method/disintegration test method of the 15$^{th}$ Revised Japanese Pharmacopoeia test methods".

(c) Degree of Wearing

The degree of wearing (percentage of a mass loss to an initial mass) was calculated after 100 revolutions (24 to 26 rpm) by using the number of tablets equivalent to an amount as close to as a total mass of 6.5 g as test samples.

This was measured in accordance with the "reference information/tablet wear degree testing method of the 15$^{th}$ revised Japanese Pharmacopoeia test methods".

$$\text{Degree of wearing } (\%) = \frac{\langle\langle <i> (g) - <ii> (g) \rangle\rangle \times 100}{<iii>}$$

<i>: initial mass of tablet before wearing test
<ii>: mass of tablet after wearing test
<iii>: initial mass of tablet before wearing test (d) Thickness of Tablet The thickness of the tablet was measured by using a thickness gauge (of Niigata Seiki Co., Ltd.).

[Preparation of Pestle Shape]

To confirm the effectiveness of the pestle shape of the present invention, change the corner angle to 15°, 30° and 45° and the cup depth to various values, and prepare three different tablets which were 250 mg, 330 mg and 500 mg in weight, pestles having a shape shown in Table 1 below were designed and prepared.

The term "corner angle single-R" in the table means a shape having a corner angle and a domed top portion with a single curvature (R) as shown in FIG. 1.

The term "single-R (comparative)" as a pestle shape in Tables 2 to 4 means a shape having no corner angle (therefore, there is no corner horizontal length) and a domed curve which is formed directly from the horizontal surface and has a curvature R.

TABLE 1

| List of corner angle single-R pestle shapes | | | | | | | | | |
|---|---|---|---|---|---|---|---|---|---|
| Type of pestle | corner angle single-R | | | | | | | | |
| Name of formulation | 250 mg formulation | | | 330 mg formulation | | | 500 mg formulation | | |
| Diameter of pestle | φ 8.0 mm | | | φ 9.0 mm | | | φ 10.5 mm | | |
| Cup depth | 0.78 mm | | | 0.87 mm | | | 1.02 mm | | |
| R (mm) | 8.8 | 12.8 | 14.9 | 10.0 | 14.7 | 17.0 | 11.6 | 17.2 | 19.9 |
| Corner angle | 15° | 30° | 45° | 15° | 30° | 45° | 15° | 30° | 45° |

[Preparation Of Formulation Sample]

The following three different samples were prepared as samples for experiments. Magnesium oxide particles having an average secondary particle diameter of 6.5 μm were used.
(1) 250 mg Formulation:

To prepare the 250 mg formulation, 20 kg of magnesium oxide particles, 1.44 kg of crystalline cellulose, 0.72 kg of croscarmellose sodium and 0.40 kg of corn starch were mixed together by means of a container type mixer, and the resulting mixture was granulated by means of a roll molding type granulator. 22.56 kg of the obtained granules having a diameter of 0.3 to 0.4 mm and 0.24 kg of calcium stearate were mixed together by means of a container type mixer to obtain granules to be tableted.
(2) 330 mg Formulation:

To prepare the 330 mg formulation, 20 kg of magnesium oxide particles, 1.39 kg of crystalline cellulose, 0.67 kg of croscarmellose sodium and 0.42 kg of corn starch were mixed together by means of a container type mixer, and the resulting mixture was granulated by means of a roll molding type granulator. 22.48 kg of the obtained granules having a diameter of 0.3 to 0.4 mm and 0.24 kg of calcium stearate were mixed together by means of a container type mixer to obtain granules to be tableted.
(3) 500 mg Formulation:

To prepare the 500 mg formulation, 20 kg of magnesium oxide particles, 1.38 kg of crystalline cellulose and 0.69 kg of croscarmellose sodium were mixed together by means of a container type mixer, and the resulting mixture was granulated by means of a roll molding type granulator. 22.07 kg of the obtained granules having a diameter of 0.3 to 0.4 mm and 0.23 kg of calcium stearate were mixed together by means of a container type mixer to obtain granules to be tableted.

Examples 1 to 4 and Comparative Examples 1 and 2

250 mg formulations were compression molded by using a rotary tableting machine [the PH-300 rotary press of Mori-Korsch Co., Ltd., VIRGO small-sized high-speed tableting machine of Kikusui Co., Ltd.], a single pestle and an open feed shoe at the revolution of a spinning disk. A compression molded product obtained by using a single-R pestle was used as comparative.

The mass of each tablet was adjusted to 287 mg, the thickness of the tablet was adjusted to 4.4 mm, and the physical properties of the tablets are shown in Table 2.

Examples 5 to 7 and Comparative Examples 3 and 4

330 mg formulations were compression molded at a spinning disk revolution of 35 rpm under the same tableting conditions as in Examples 1 to 4. The mass of each tablet was adjusted to 377 mg, the thickness of the tablet was adjusted to 4.7 mm, and the physical properties of the tablets are shown in Table 3.

TABLE 3

Physical properties of 330 mg formulations

|  | Comp. Ex. 3 | Ex. 5 | Ex. 6 | Ex. 7 | Comp. Ex. 4 |
|---|---|---|---|---|---|
| Pestle shape | *1 | *1 | *1 | *1 | *2 |
| Pestle diameter | φ 9.0 mm | φ 9.0 mm | φ 9.0 mm | φ 9.0 mm | φ 9.0 mm |
| Corner angle | 15° | 30° | 45° | 30° | — |
| Corner horizontal length | 0.93 mm | 0.68 mm | 0.39 mm | 0.68 mm | — |
| Cup depth | 0.87 mm | 0.87 mm | 0.87 mm | 0.87 mm | 0.77 mm |
| R | 10.0 | 14.7 | 17.0 | 14.7 | 13.0 |
| Tableting pressure (KN) | 12 | 8 | 7 | 9 | 9 |
| Tablet hardness (N) | 169 | 140 | 128 | 130 | 130 |
| Degree of wearing (%) | 0.37 | 0.25 | 0.21 | 0.27 | 0.56 |

*1: corner angle single-R
*2: single-R (comparative)
Magnesium oxide particles containing a solid solution of Zn were used in Example 7.

Examples 8 to 11 and Comparative Examples 5 and 6

500 mg formulations were compression molded at a spinning disk revolution of 35 rpm under the same tableting conditions as in Examples 1 to 4. The mass of each tablet was adjusted to 580 mg, the thickness of the tablet was adjusted to 5.1 mm, and the physical properties of the tablets are shown in Table 4.

TABLE 2

Physical properties of 250 mg formulations

|  | Comp. Ex. 1 | Ex. 1 | Ex. 2 | Ex. 3 | Ex. 4 | Comp. Ex. 2 |
|---|---|---|---|---|---|---|
| Pestle shape | *1 | *1 | *1 | *1 | *1 | *2 |
| Pestle diameter | φ 8.0 mm | φ 8.0 mm | φ 8.0 mm | φ 8.0 mm | φ 8.0 mm | φ 8.0 mm |
| Corner angle | 15° | 30° | 30° | 45° | 30° | — |
| Corner horizontal length | 0.78 mm | 0.61 mm | 0.61 mm | 0.35 mm | 0.61 mm | — |
| Cup depth | 0.78 mm | 0.78 mm | 0.65 mm | 0.78 mm | 0.78 mm | 0.65 mm |
| R | 8.8 | 12.8 | 18.2 | 14.9 | 12.8 | 12.0 |
| Tableting pressure (KN) | 12 | 9 | 7 | 8 | 8 | 9 |
| Tablet hardness (N) | 123 | 127 | 62 | 113 | 110 | 114 |
| Degree of wearing (%) | 0.47 | 0.19 | 0.11 | 0.19 | 0.15 | 0.29 |

*1: corner angle single-R
*2: single-R (comparative)
Magnesium oxide particles containing a solid solution of Zn ($Mg_{0.7}Zn_{0.3}$) were used in Example 4 (the same shall apply hereinafter).

TABLE 4

Physical properties of 500 mg formulations

|  | Comp. Ex. 5 | Ex. 8 | Ex. 9 | Ex. 10 | Ex. 11 | Comp. Ex. 6 |
|---|---|---|---|---|---|---|
| Pestle shape | *1 | *1 | *1 | *1 | *1 | *2 |
| Pestle diameter | φ 10.5 mm | φ 10.5 mm | φ 10.5 mm | φ 10.5 mm | φ 10.5 mm | φ 10.5 mm |
| Corner angle | 15° | 30° | 45° | 30° | 30° | — |
| Corner horizontal length | 1.12 mm | 0.80 mm | 0.46 mm | 0.80 mm | 0.80 mm | — |
| Cup depth | 1.02 mm | 1.02 mm | 1.02 mm | 0.94 mm | 1.02 mm | 0.78 mm |
| R | 11.6 | 17.2 | 19.9 | 20.0 | 17.2 | 17.5 |
| Tableting pressure (KN) | 23 | 16 | 14 | 16 | 16 | 13 |
| Tablet hardness (N) | 197 | 186 | 178 | 135 | 180 | 181 |
| Degree of wearing (%) | 0.89 | 0.30 | 0.35 | 0.54 | 0.42 | 1.03 |

*1: corner angle single-R
*2: single-R (comparative)
Magnesium oxide particles containing a solid solution of Zn were used in Example 11.

Examples 12 to 14

A stabilization test was carried out by using the 250 mg formulations, the 330 mg formulations and the 500 mg formulations obtained in Examples 1, 5 and 8. The test was conducted in a glass bottle (airtight) at 40° C. for one month. The results are shown in Table 5.

TABLE 5

Stabilization test

|  | Ex. 12 | | Ex. 13 | | Ex. 14 | |
|---|---|---|---|---|---|---|
| Example No. of formulation | Ex. 1 | | Ex. 5 | | Ex. 8 | |
| Name of formulation | 250 mg | | 330 mg | | 500 mg | |
| Storage condition | 40° C. | | 40° C. | | 40° C. | |
| Measurement time | Initial | after 1 month | Initial | after 1 month | Initial | after 1 month |
| Mass (mg) | 287 | 289 | 380 | 384 | 581 | 574 |
| Thickness of tablet (mm) | 4.40 | 4.41 | 4.72 | 4.73 | 5.12 | 5.10 |
| Hardness of tablet (N) | 73 | 106 | 89 | 133 | 116 | 151 |
| Disintegration time (sec.) | 8 | 7 | 9 | 8 | 10 | 8 |

Constant temperature and humidity tank: LH-21 11M (of Nagano Science)
Storage state: glass bottle (airtight)

DESCRIPTION OF REFERENCE NUMERALS

1 center line
2-*a* upper horizontal surface
2-*b* lower horizontal surface
3-*a* surrounding side surface
3-*b* surrounding side surface
4-*a* upper dome horizontal surface
4-*b* lower dome horizontal surface
5 diameter
6 thickness
7 cup depth
8 linear side
9 corner horizontal length
10 upper pestle
10-*a* end of upper pestle
11 mortar
12 lower pestle
12-*a* end of lower pestle
θ corner angle
R domed curve

The invention claimed is:

1. A tablet having a domed shape on upper and lower horizontal surfaces of a cylindrical plate shape, which comprises magnesium oxide particles represented by the following formula (1) as the main component,

$$(Mg_{1-x}Zn_x)O \qquad (1)$$

wherein x is 0 to 0.3, the content of the magnesium oxide particles being 85 to 95 wt %,
wherein:
the domed shape has a two-stage structure consisting of a linear portion from both ends of a horizontal surface and part of a circle having a curvature R in a cross-section,
the linear portion has an angle of 25° to 45° and a corner horizontal length of 0.3 mm to 1.0 mm,
the part of the circle having a curvature R has a radius of from 7 mm to 25 mm, and a cup has a depth of 0.6 mm to 1.2 mm.

2. The tablet according to claim 1, wherein the linear portion has an angle of 28 to 40°.

3. The tablet according to claim 1, wherein the corner horizontal length is 0.35 to 0.85 mm.

4. The tablet according to claim 1, wherein the cup has a depth of 0.65 to 1.1 mm.

5. The tablet according to claim 1, wherein the length (diameter) of the horizontal surface of the cross-sectional shape is 7 to 11 mm.

6. The tablet according to claim 1 which comprises magnesium oxide particles having an average secondary particle diameter of 0.5 to 25 μm as the main component.

7. The tablet according to any one of claims 1 to 5 and 6 which is administered orally.

8. The tablet according to any one of claims 1 to 5 and 6 which is used for laxative purpose.

9. The tablet according to any one of claims 1 to 5 and 6 which is used for laxative purpose and administered orally.

10. A tablet configured for oral administration and suitable for use as a laxative, said tablet having a domed shape on upper and lower horizontal surfaces of a cylindrical plate shape, which tablet comprises as a main component magnesium oxide particles having an average secondary particle diameter of 0.5 to 25 μm, said magnesium oxide particles being represented by formula (1)

$$(Mg_{1-x}Zn_x)O \tag{1}$$

wherein x is 0 to 0.3, the content of the magnesium oxide particles in said tablet being 85 to 95 wt %, wherein:
- the domed shape has a two-stage structure consisting of a linear portion from both ends of a horizontal surface and part of a circle having a curvature R in a cross-section, the length of the horizontal surface of the cross-section shape being 7 to 11 mm,
- the linear portion has an angle of 28° to 40° and a corner horizontal length of 0.35 mm to 0.85 mm,
- the part of the circle having a curvature R has a radius of from 7 mm to 25 mm, and
- a cup depth, defined as the distance from a horizontal surface of the tablet to the apex of the domed shape, has a depth of 0.65 mm to 1.1 mm.

* * * * *